(12) United States Patent
Hamlekhan et al.

(10) Patent No.: US 11,484,366 B2
(45) Date of Patent: Nov. 1, 2022

(54) ADAPTER ASSEMBLY TO ENABLE NAVIGATION FOR ENT INSTRUMENTS

(71) Applicant: Acclarent, Inc., Irvine, CA (US)

(72) Inventors: Azhang Hamlekhan, Irvine, CA (US); Jetmir Palushi, Irvine, CA (US); John H. Thinnes, Jr., Mission Viejo, CA (US); Krishna Murthy Rajan, Irvine, CA (US); George L. Matlock, Pleasanton, CA (US)

(73) Assignee: Acclarent, Inc., Irvine, CA (US)

( * ) Notice: Subject to any disclaimer, the term of this patent is extended or adjusted under 35 U.S.C. 154(b) by 412 days.

(21) Appl. No.: 16/584,976

(22) Filed: Sep. 27, 2019

(65) Prior Publication Data
US 2020/0170717 A1 Jun. 4, 2020

Related U.S. Application Data

(60) Provisional application No. 62/772,674, filed on Nov. 29, 2018.

(51) Int. Cl.
*A61B 17/24* (2006.01)
*A61B 17/00* (2006.01)
(Continued)

(52) U.S. Cl.
CPC .............. *A61B 34/20* (2016.02); *A61B 17/24* (2013.01); *A61B 2017/00486* (2013.01); *A61B 2034/2051* (2016.02); *A61M 25/09* (2013.01)

(58) Field of Classification Search
CPC ........... A61M 2025/09125; A61M 2025/0166; A61M 25/09; A61M 2025/0915; A61M 2025/09175; A61M 2025/0687; A61M 2025/0188; A61M 25/0905; A61M 25/01; A61B 2090/0817; A61B 2034/2072;
(Continued)

(56) References Cited

U.S. PATENT DOCUMENTS 5,456,680 A * 10/1995 Taylor .................. A61B 18/245
606/7
6,605,062 B1 * 8/2003 Hurley ................ A61M 25/104
604/164.13
(Continued)

FOREIGN PATENT DOCUMENTS

WO     WO 2018/169128 A1     9/2018

OTHER PUBLICATIONS

Partial European Search Report dated Apr. 15, 2020 for Application No. 19212053.3, 14 pages.
(Continued)

*Primary Examiner* — Jocelin C Tanner
(74) *Attorney, Agent, or Firm* — Frost Brown Todd LLC

(57) ABSTRACT

An apparatus includes a proximal portion and a distal portion attached to the proximal portion. The proximal portion includes a proximal surface. The proximal portion defines a first pathway and a second pathway that both extend distally from the proximal surface. The first pathway is dimensioned to receive a shaft while the second pathway is dimensioned to receive a navigation guidewire. The distal portion includes a distal tip terminating into a distal end. The second pathway extends from the proximal portion into the distal tip.

17 Claims, 8 Drawing Sheets

(51) Int. Cl.
*A61M 25/09* (2006.01)
*A61B 34/20* (2016.01)

(58) Field of Classification Search
CPC .... A61B 2034/2065; A61B 2034/2051; A61B 2017/00946; A61B 2017/00862; A61B 2017/00486; A61B 2017/00477; A61B 2017/00473; A61B 34/20; A61B 17/24
See application file for complete search history.

(56) References Cited

U.S. PATENT DOCUMENTS

| | | | |
|---|---|---|---|
| 7,720,521 B2 | 5/2010 | Chang et al. | |
| 10,561,370 B2 | 2/2020 | Salazar et al. | |
| 2002/0169502 A1* | 11/2002 | Mathis | A61B 17/3421 623/2.11 |
| 2003/0050600 A1* | 3/2003 | Ressemann | A61B 17/22 604/101.01 |
| 2005/0209533 A1* | 9/2005 | Lorenz | A61M 25/09 604/528 |
| 2006/0063973 A1* | 3/2006 | Makower | A61B 1/018 600/114 |
| 2009/0069802 A1* | 3/2009 | Garito | A61B 18/14 606/49 |
| 2010/0152720 A1* | 6/2010 | Sauro | A61B 18/24 606/14 |
| 2013/0172673 A1 | 7/2013 | Kennedy, II et al. | |
| 2014/0364725 A1 | 12/2014 | Makower | |
| 2015/0080764 A1 | 3/2015 | Poe | |
| 2016/0008083 A1* | 1/2016 | Kesten | A61B 34/20 600/424 |
| 2017/0119473 A1* | 5/2017 | Clopp | A61M 25/09 |
| 2018/0085174 A1 | 3/2018 | Radtke et al. | |
| 2018/0099125 A1* | 4/2018 | Richer | A61B 34/20 |
| 2018/0104001 A1* | 4/2018 | Palushi | A61B 18/1206 |

OTHER PUBLICATIONS

European Search Report and Written Opinion dated Jul. 20, 2020 for Application No. 19212053.3, 12 pages.

* cited by examiner

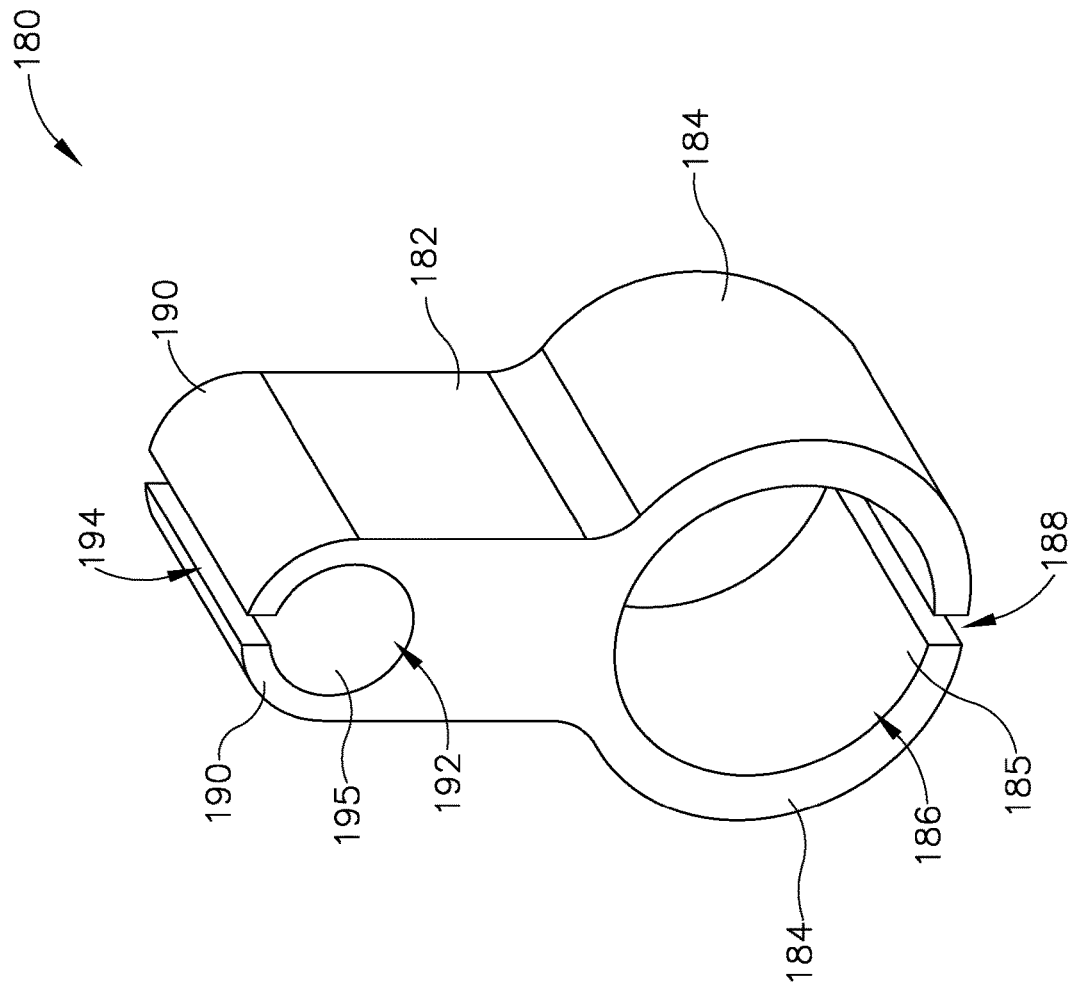

ADAPTER ASSEMBLY TO ENABLE NAVIGATION FOR ENT INSTRUMENTS

PRIORITY

This application claims priority to U.S. Provisional Pat. App. No. 62/772,674, entitled "Adapter Assembly to Enable Navigation for ENT Instruments," filed Nov. 29, 2018, the disclosure of which is incorporated by reference herein.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 8 depicts a perspective view of an exemplary alternative wire retainer clip that may be readily incorporated into the image guided adaptor assembly of FIG. 2.

Figure 1:
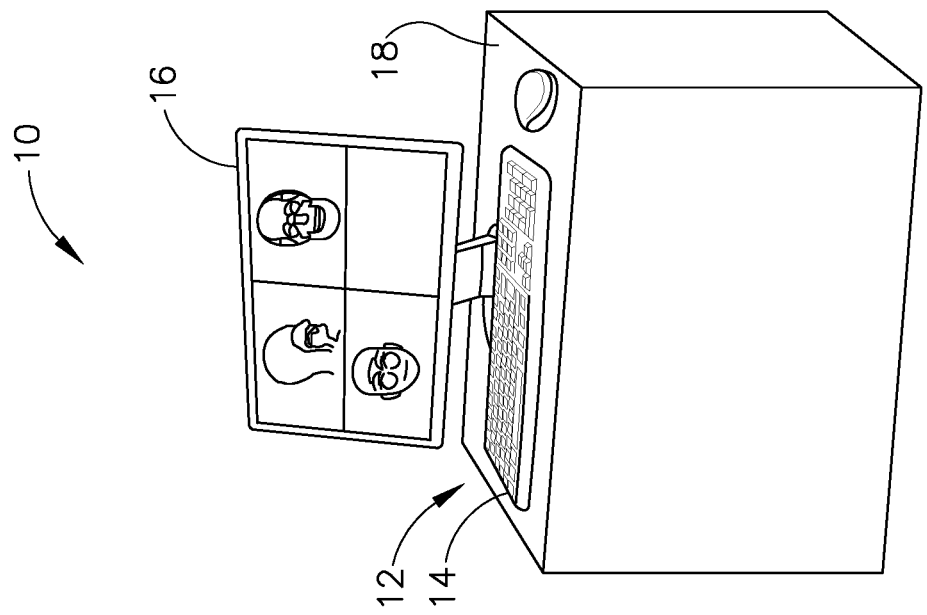
FIG. 1 depicts a schematic view of an exemplary surgery navigation system being used on a patient seated in an exemplary medical procedure chair.
Figure 1:
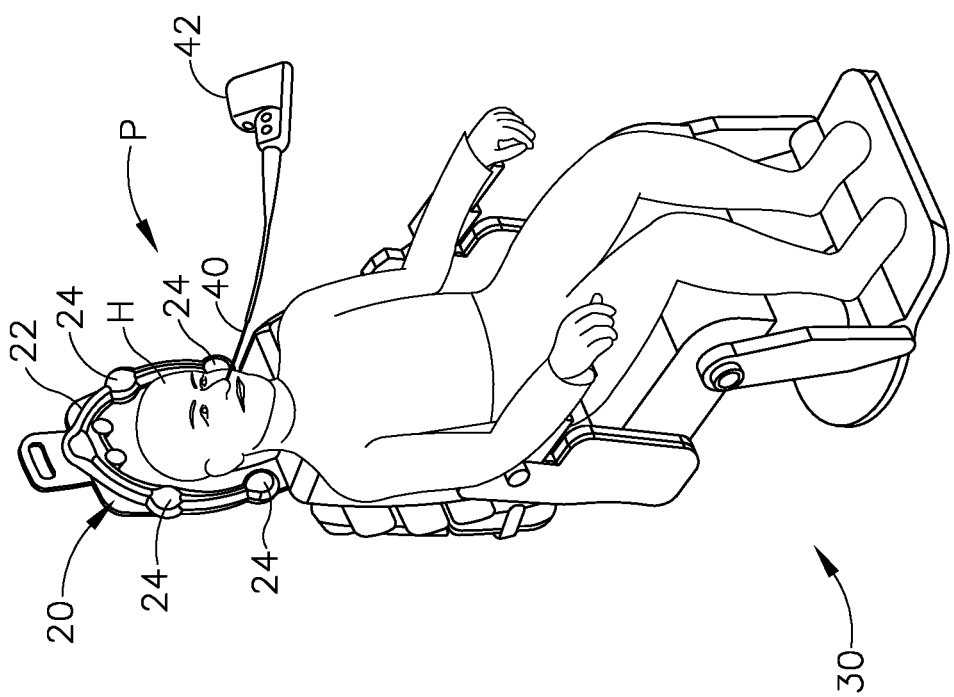

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Exemplary Image Guided Surgery Navigation System

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," (now abandoned) published Dec. 11, 2014, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. patent application Ser. No. 15/933,737, entitled "Apparatus to Secure Field Generating Device to Chair," filed Mar. 23, 2018, issued as U.S. Pat. No. 10,561,370 on Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (16).

The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a sensor like the sensor of navigation guidewire (40).

II. Exemplary Image Guided Instrument Assembly

In some instances, it may be desirable modify an instrument, previously without IGS navigation capabilities, to be used in conjunction with IGS navigation system (10). In other words, it may be desirable to quickly modify an instrument that has no prior IGS navigation capabilities such that when the modified instrument is used, the real-time spatial position of at least portions of the modified instrument (such as the distal end) a may be visualized on screen (16) in accordance with the description above. Further, it may be desirable to modify an instrument, previously without IGS capabilities, with various distal tips that may be used in conjunction with IGS navigation system (10). Therefore, a single instrument may be modified to have distal tips with various geometries, thereby serving various purposes. Additionally, each distal tip, or at least a portion thereof, may be visualized on screen (16) during exemplary use in accordance with the description above.

Figure 2:
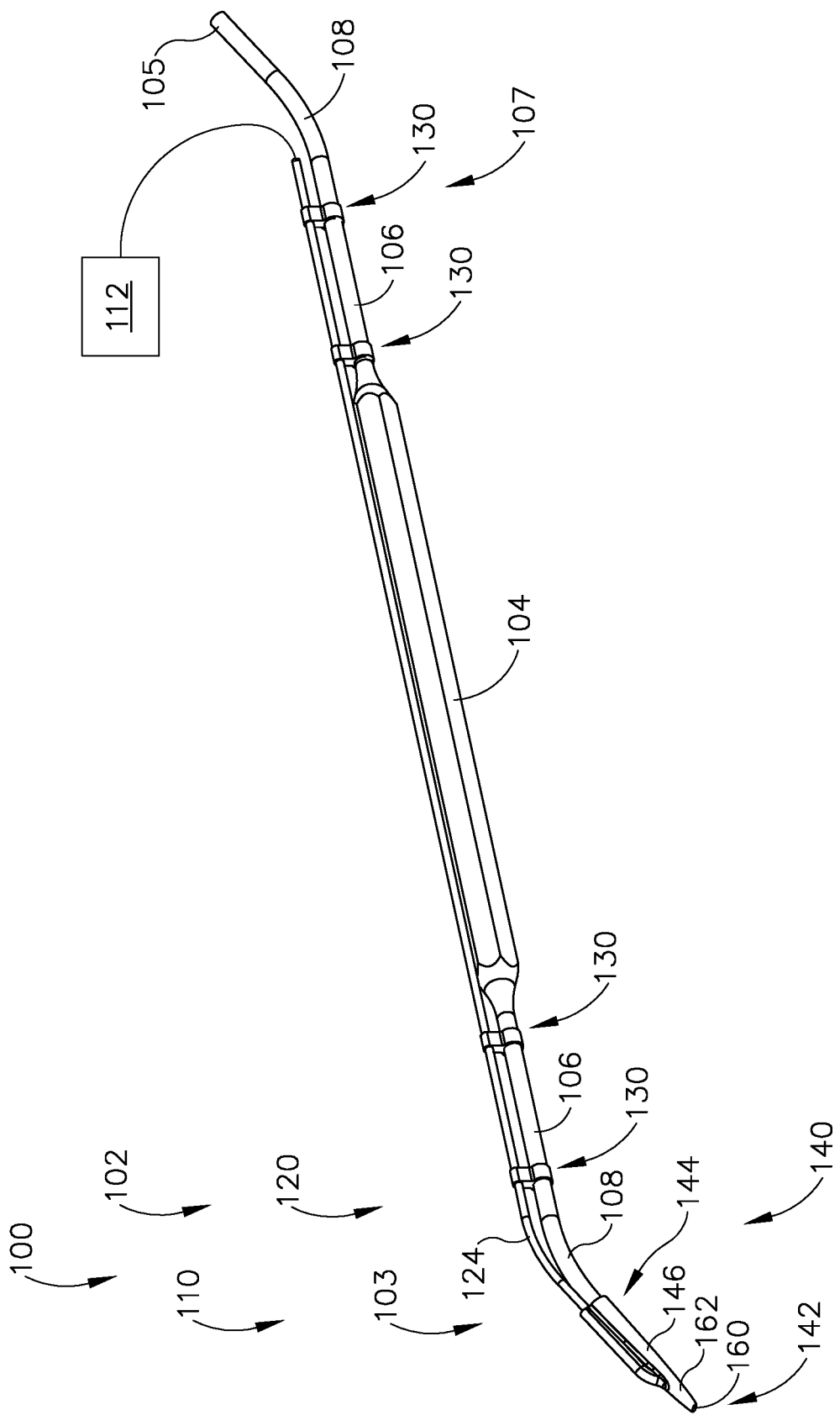
FIG. 2 depicts a perspective view of an exemplary image guided instrument assembly that may be readily incorporated into the surgery navigation system of FIG. 1, including a surgical instrument and an image guided adaptor assembly.

FIG. 2 shows an exemplary image guided instrument assembly (100) including a surgical instrument (102) and an image guided adapter assembly (110). Surgical instrument (102), by itself, may be incompatible for use with IGS navigation system (10). Of course, it is envisioned that in some examples, surgical instrument (102), or selected portions of surgical instrument (102), may be compatible for use with IGS navigation system (10). As will be described in greater detail below, image guided assembly (110) may selectively attach to surgical instrument (102) to provide use of surgical instrument (102) with IGS navigation system (10) in replacement of navigation guidewire (40) and coupling unit (42) described above. Additionally, as will be described in greater detail below, various adaptor bodies (140) having various tip geometries may be attached to a distal end (103) of instrument (102) to provide various end effector functionalities that are also compatible with IGS navigation system (10).

Surgical instrument (102) includes a handle (104) with a shaft (106) extending away from each end of handle (104). Shafts (106) are dimensioned to be transnasally inserted in head (H) of patient (P) such that a free end (105) of shaft (106) may access a desired nasal passageway. Of course, this is merely optional, as shaft (106) may be dimensioned for insertion into any relevant portion of patient as would be apparent to one having ordinary skill in the art in view of the teachings herein.

One shaft (106) extends toward a proximal end (107), while another shaft (106) extends toward a distal end (103). In the present example, each shaft (106) terminates at free end (105). Additionally, in the present example, each shaft (106) includes a bend (108) located between free end (105) and a substantially linear portion of shaft (106) that is closer to handle (104). Bend (108) may form an angle relative to the longitudinal axis defined by the substantially linear portion of shaft (106) such that free end (105) may access a desired nasal cavity. Bend (108) may form any suitable angle relative to the longitudinal axis of the substantially liner portion of shaft (106) as would be apparent to one having ordinary skill in the art in view of the teachings herein. Of course, it is imagined in some instances, bend (108) may be entirely omitted.

In the current example, free end (105) has a substantially cylindrical geometry such that free ends (105) include a generally flat circular surface. It should be understood that free end (105) may have any suitable geometry as would be apparent to one having ordinary skill in the art in view of the teachings herein. For example, free end (105) may have a sharp pointed end to function as a piercing tip. Alternatively, free end (105) may have a suitable geometry required to function as a Cottle elevator, a freer, a seeker, a curette, etc.

In the current example, shaft (106) is rigid. However, it should be understood that any suitable portion of shaft (106) may be malleable. For example, the portion of shaft (106) forming bend (108) may be malleable such that bend (108) may be manipulated to change the angle defined relative to the substantially linear portion of shaft (106). Therefore, shaft (106) may be modified to access different nasal cavities. However, while bend (108) may be malleable, bend (108) may still be sufficiently rigid such that bend (108) does not deform when inserted within head (H) of patient (P).

In the current example, there are two shafts (106) having free ends (105) that are angularly offset from each other by 180 degrees about the longitudinal axis of handle (104), with similar angle of bends (108) and geometries of free ends (105) compared to each other. However, this is merely optional. It should be understood that in some embodiments only one shaft (106) may extend from handle (104). In other embodiments, two shafts (106) may extend form handle (104), but with different angles of bends (108), and/or different geometries of free ends (105). Of course, any suitable type of shaft (106) may be utilized with any suitable type of bend (108) and free end (105) as would be apparent to one having ordinary skill in the art in view of the teachings herein.

Image guided adapter assembly (110) includes a coupling unit (112), a navigation guidewire (120), a plurality of wire retainer clips (130), and adaptor body (140). As mentioned above, and as will be described in greater detail below, image guided assembly (110) may selectively attach to surgical instrument (102) to provide use of surgical instrument (102) in conjunction with IGS navigation system (10). As also mentioned above, and as will be described in greater detail below, adaptor body (140) may attach to distal end (103) of free end (105) in order to perform various end effector functions while also coupling with a distal end of navigation guidewire (120), thereby providing use of surgical instrument (102) in conjunction with IGS navigation system (10).

Navigation guidewire (120) and coupling unit (112) may be substantially similar to navigation guidewire (40) and coupling unit (42) described above, respectively, with differences elaborated below. A proximal end of navigation guidewire (120) is in communication with coupling unit (112). A proximal end of navigation guidewire (120) may be configured to selectively attach to coupling unit (112). Guidewire (120) and coupling unit (112) may couple using any suitable methods as would be apparent to one having ordinary skill in the art in view of the teachings herein. Alternatively, a proximal end of navigation guidewire (120) may be affixed to coupling unit (112). Coupling unit (112) is configured to provide communication of data and other signals between console (18) and navigation guidewire (120). Coupling unit (112) may provide wired or wireless communication of data and other signals.

Navigation guidewire (120) includes a distal position sensor (122) and a flexible electrical conduit assembly (124) extending proximally from distal position sensor (122). Position sensor (122) is substantially similar to position sensor of navigation guidewire (40) described above. Therefore, position sensor (122) comprises at least one coil. Additionally, flexible electrical conduit assembly (124) includes electrical conduit(s) in communication with at least one coil of position sensor (122). Flexible electrical conduit assembly (124) may be substantially flexible such that navigation guidewire (120) may conform along the profile shaft (106) and handle (104) of instrument in accordance with the description herein. Flexible electrical conduit assembly (124) may include some type of coating/insulating material to shield the electrical conduit(s) from the external environment.

If coil(s) of position sensor (122) is positioned within an alternating electromagnetic field generated by field generators (24), the alternating magnetic field may generate electrical current in the coil of position sensor (122), and this electrical current may be communicated along flexible electrical conduit assembly (124) in navigation guidewire (120) and further to processor (12) via coupling unit (112). Therefore, processor (12) may determine the location of position sensor (122) in similar fashion to position sensor of navigation guidewire (40) described above.

Wire retainer clips (130) are configured to couple navigation guidewire (120) with instrument (102). In particular, retainer clips (130) are configured to couple flexible electrical conduit assembly (124) of navigation guidewire (120) with shafts (106) of instrument (102) such that navigation guidewire (120) extends along the profile of instrument (102) without interfering with suitable access to handle (104). Therefore, the operator may suitably grasp and control image guided instrument assembly (100) via handle (104) without being unduly obstructed from the presence of navigation guidewire (120) extending proximally toward coupling unit (112).

Figure 3:
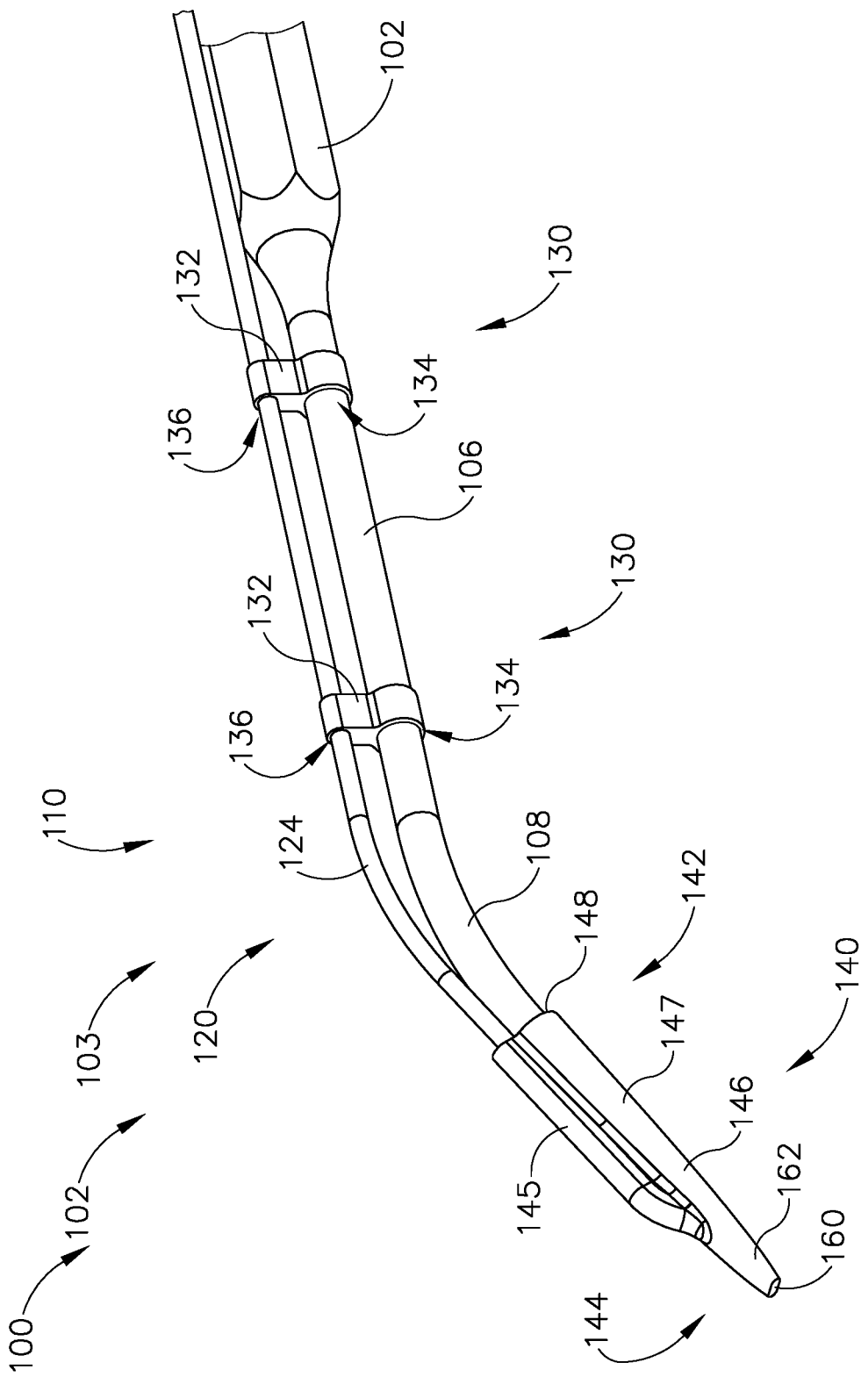
FIG. 3 depicts a perspective view of a distal end of the image guided instrument assembly of FIG. 2.
Figure 5:
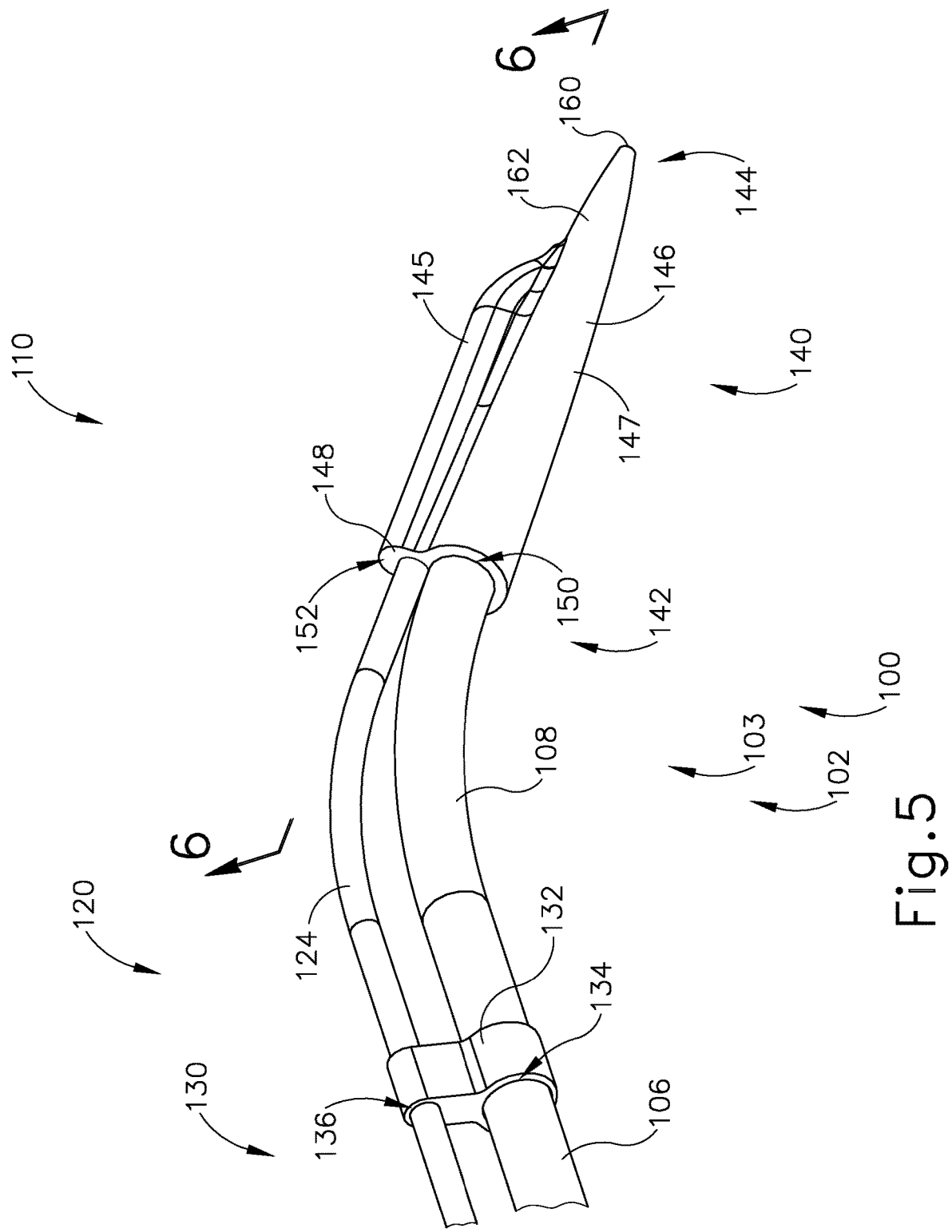
FIG. 5 depicts another perspective view of the distal end of the image guided instrument assembly of FIG. 2.

Retainer clips (130) include a body (132) that defines a shaft through hole (134) and guidewire through hole (136). Retainer clips (130) may be attached to shaft (106) by inserting shaft through holes (134) over free ends (105) and are further sliding retainer clips (130) into position, as exemplified in FIGS. 2-3, and 5. Retainer clips (130) may be attached to navigation guidewire (120) by inserting either the proximal end of navigation guidewire (120) or the distal end of navigation guidewire (120) into guidewire through holes (136) until navigation guidewire (120) is in the desired position.

Figure 4:
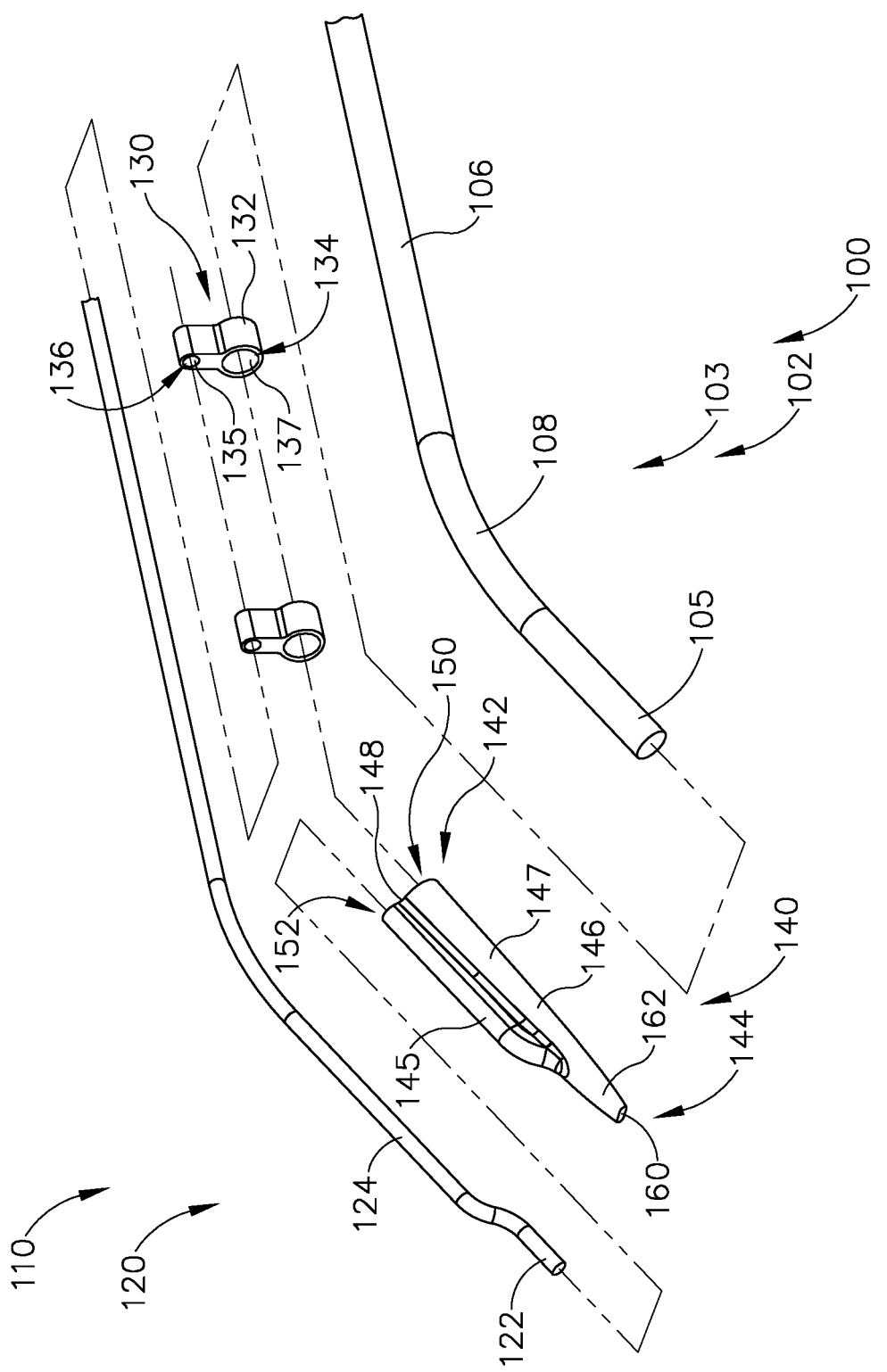
FIG. 4 depicts an exploded perspective view of the distal end of the image guided instrument assembly of FIG. 2.
Figure 7:
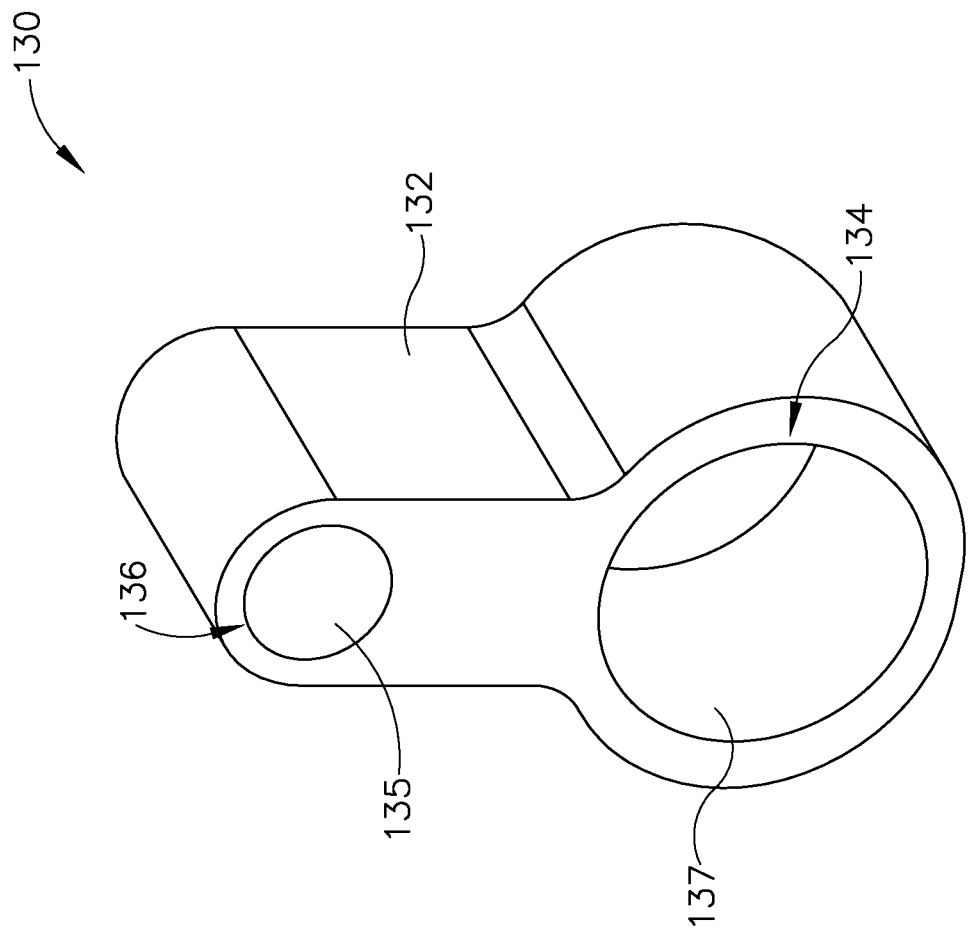
FIG. 7 depicts a perspective view of an exemplary wire retainer clip of the image guided adaptor assembly of FIG. 2.

As best seen in FIGS. 4 and 7, a first interior annular surface (135) of body (132) defines shaft through hole (134), while a second interior annular surface (137) of body (132) defines guidewire through hole (136). First interior annular surface (135) and second interior annular surface (137) are dimensioned and configured to couple with respective shaft (106) or guidewire (120) via a suitable friction interference fitting such that shaft (106) and guidewire (120) do not move relative to retainer clips (130) during exemplary use, but also such that guidewire (120) and shaft (106) may couple/decouple from retainer clips (130) under sufficient force when the operator desires to assemble or disassemble retainer clips (130) from shaft (106) and/or guidewire (120). First interior annular surfaces (135) and second interior annular surface (137) may include any suitable material for a friction inference fitting as would be apparent to one having ordinary skill in the art in view of the teachings herein. For example, interior annular surfaces (135, 137) may include an elastomeric material.

FIG. 8 shows an alternative wire retainer clip (180) that is configured to function substantially similar to wire retainer clip (130) described above, with differences elaborated below. In particular, retainer clip (180) includes a body (182) having pairs of resilient arched arms (184, 190). Each pair of resilient arched arms (184, 190) include respective interior semi-annular surfaces (186, 195) that define shaft through hole (186) and guide wire through hole (192), respectively. Resilient arched arms (184) define a gap (188) while resilient arched arms (190) define another gap (194). Resilient arched arms (184, 190) may flex away from respective gaps (188, 194) under sufficient force, such as when the operator attempts to couple/decouple guidewire (120) or shaft (106) in accordance with the description herein. Additionally, resilient arched arms (184, 190) are dimensioned to selectively fix to shaft (106) and navigation guidewire (120) during exemplary use via the friction fitting provided by the resilient nature of arched arms (184, 190). Interior semi-annular surfaces (186, 195) may also include a material to help promote a friction interference fitting, such as an elastomeric material.

Figure 6:
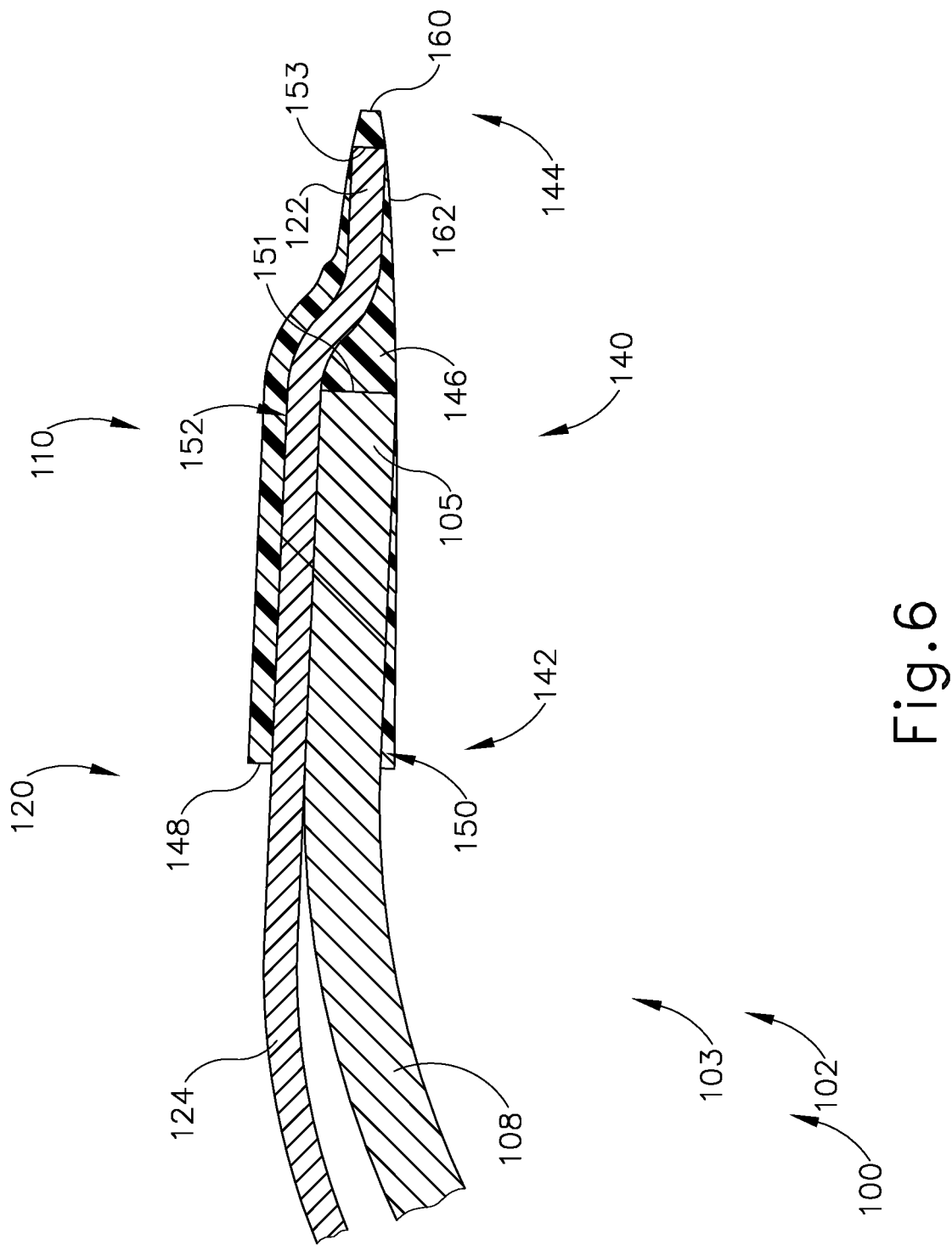
FIG. 6 depicts a cross-sectional view, taken along line 6-6 of FIG. 5, of the distal end of the image guided instrument assembly of FIG. 2.

Adaptor body (140) extends between a proximal portion (142) and a distal portion (144). Adaptor body (140) includes a shaft portion (147), a guidewire portion (145), and a distal tip (162) terminating into a distal end (160). The proximal end of shaft portion (147) and guidewire portion (145) of adaptor body (140) include a proximally facing surface (148) that defines a shaft pathway (150) and a wire pathway (152). As best seen in FIG. 6, shaft pathway (150) extends into adaptor body (140) toward distal portion (144) and terminates into a distal surface (151). Shaft pathway (150) is dimensioned to receive free end (105) of shaft (106). Free end (105) may be inserted into shaft pathway (150) until free end (105) abuts against distal surface (151), although this is merely optional.

Wire pathway (152) extends into adaptor body (140) into the confines of distal tip (162) and terminates into a distal surface (153). Wire pathway (152) extends adjacent to shaft pathway (150), then distally past shaft pathway (150) into distal tip (162). Position sensor (122) may be inserted into wire pathway (152) until a distal end of position sensor (122) abuts against distal surface (153), although this is merely optional. Wire pathway (152) extends into adaptor body (140) such that position sensor (122) may be inserted suitably close to a distal end (160) of distal tip (162). Therefore, when suitably assembled, position sensor (122) may accurately indicate the position of distal tip (162) during exemplary use in accordance with the description herein. Shaft pathway (150) and wire pathway (152) may be isolated relative to each other, or may be in communication with each other, yet still dimensioned to selectively receive shaft (106) and position sensor (122), respectively.

Adaptor body (140) is configured to couple relative to free end (105) of shaft (106) as well as position sensor (122) of navigation guidewire (120) such that when assembled, navigation guidewire (120), adaptor body (140), and free end (105) are fixed relative to each other via an interference fit. The interference fit between adaptor body (140), free end (105) of shaft (106), and position sensor (122) may be strong enough such that free end (105), position sensor (122), and adaptor body (140) are fixed relative to each other during exemplary use, but weak enough such that the operator may selectively decouple adaptor body (140) form position sensor (122) and free end (105) of shaft (106) when desired.

Position sensor (122) may be easily and repeatably located at distal tip (162) of adaptor body (140). Therefore, suitable portions of adaptor body (140) may be sufficiently flexible to fixedly receive position sensor (122) and free end of shaft (105) via an interference fit. In some instances, adaptor body (140) may have pathways (150, 152) lined with an elastomeric material to further promote an interference fit. In some instances, pathways (150, 152) and/or free end (105) and position sensor (122) may have resilient clips to provide tactile feedback when free end (105) and position sensor (122) suitably couple with adaptor body (140) and to ensure free end (105) and position sensor (122) remain fixed relative to adaptor body (140) during exemplary use. In some instances, pathways (150, 152) and corresponding features of free end (105) and position sensor (122) may include complementary keyed features to make sure adaptor body (140) is rotationally aligned with free end (105) and/or position sensor (102) when assembled.

Distal tip (162) of adaptor body (140) is sufficiently rigid to act as an end effector and perform desired functions within patient (P). In some instances, adaptor body (140) is made from a single material such that adaptor body is sufficiently rigid to act as an end effector, yet sufficiently flexible to tightly couple with guide wire (120) and free end (105) of shaft (106). In some instances, adaptor body (140) is manufactured through moldings, machining processes, 3D printing, or any other suitable manufacturing method as would be apparent to one having ordinary skill in the art in view of the teachings herein. In some instances, adaptor body (140) is made from a variety of materials such that distal tip (162) may be sufficiently rigid, while adaptor body (1450) is also sufficiently flexible to tightly couple with guide wire (120) and free end (105) of shaft (106). Any suitable material(s) may be used as would be apparent to one having ordinary skill in the art in view of the teachings herein.

Distal tip (162) may have various geometries to perform various functions. Therefore, a plurality of adaptor bodies (140) may be used with intent (102) such that one adaptor body (140) may be attached to instrument (102) and guide wire (120) for a first purpose, then another adaptor body (140) may be attached to instrument (102) and guide wire (120) for a second purpose. Distal tip (162) may have a geometry that makes adaptor body (140) suitable to perform any suitable function as would be apparent to one having ordinary skill in the art in view of the teachings herein. For instance, distal tip (162) may have a geometry to perform the function of a seeker, a Cottle Elevator, a freer, to pierce a septum elevator, dissectors, dilators, curettes. Other examples include distal tip (162) having a geometry that is narrow and more pointed, a flat spoon-like shape, or a Cottle having more finely, sharpened, piercing tip.

Adaptor body (140) may be configured to couple with instrument (102), wherein instrument (102) is specifically designed to receive adaptor body (140). Therefore, instrument (102) may be dimensioned to specifically couple with multiple adaptor bodies (140) that perform various functions, as well as receive wire retainer clips (130) and navigation guidewire (120). Alternatively, adaptor body (140) may be configured to couple with an off-the-shelf instrument (102) in order to provide IGS capabilities to free end (105) of instrument (102). Therefore, adaptor body (140) may have any suitable dimensions necessary to suitably couple with instrument (102), regardless of the type of instrument (102) being used. Adaptor body (140) may be disposable such that after one use uses, adaptor body (140) may be thrown away. Alternatively, Adaptor body (140) may be configured to be sterilized in order to be used multiple times.

It should be understood from the foregoing that an operator may advance distal tip (162), while image guided instrument assembly (100) is suitably assembled, into various passageways within a head (H) of a patient (P) and receive real-time feedback on the location of distal tip (162) via position sensor (122) within the head (H) of the patient (P). The operator may thus maneuver distal tip (162) to explore various passageways, or perform other suitable functions, within a head (H) of a patient (P) in the context of visualization that is provided via display screen (16) of IGS navigation system (10).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a proximal portion, wherein the proximal portion comprises a proximal surface, wherein the proximal portion defines a first pathway and a second pathway, wherein the first pathway and the second pathway extend distally from the proximal surface, wherein the first pathway is dimensioned to receive a shaft, wherein the second pathway is dimensioned to receive a navigation guidewire; and (b) a distal portion attached to the proximal portion, wherein the distal portion comprises a distal tip terminating at a distal end, wherein the second pathway extends from the proximal portion into the distal tip.

Example 2

The apparatus of Example 1, wherein the distal tip comprises a seeker

Example 3

The apparatus of Example 1, wherein the distal tip comprises a Cottle Elevator.

Example 4

The apparatus of Example 1, wherein the distal tip comprises a Freer.

Example 5

The apparatus of Example 1, wherein the distal end comprises a narrow-pointed tip.

Example 6

The apparatus of Example 1, wherein the distal tip comprises a spoon-like shape.

Example 7

The apparatus of any one or more of Examples 1 through 6, wherein the proximal portion and the distal portion of formed from a first material.

Example 8

The apparatus of Example 7, wherein the first material is flexible enough to suitably attach to the shaft and the navigation guidewire.

Example 9

The apparatus of any one or more of Examples 1 through 8, wherein the first pathway terminates into a first surface.

Example 10

The apparatus of Example 9, wherein the second pathway terminates into a second surface, wherein the second surface is distal relative to the first surface.

Example 11

The apparatus of Example 10, wherein the second surface is located within the distal tip.

Example 12

An image guided adaptor assembly configured to couple with an instrument, the image guided adaptor assembly comprising: (a) a navigation guidewire; (b) a wire retainer clip, wherein the wire retainer clip is configured to couple with the navigation guidewire and a shaft of the instrument; (c) an adaptor body, wherein the adaptor body comprises: (i) a proximal portion, wherein the proximal portion comprises a proximal surface, wherein the proximal portion defines a first pathway and a second pathway, wherein the first pathway and the second pathway extend distally from the proximal surface, wherein the first pathway is dimensioned to receive a free end of the shaft, wherein the second pathway is dimensioned to receive a distal end of the navigation guidewire such that the navigation guidewire and the free end of the shaft are fixed relative to each other; and (ii) a distal portion attached to the proximal portion, wherein the distal portion comprises a distal tip terminating at a distal end, wherein the second pathway extends from the proximal portion into the distal tip.

Example 13

The image guided adaptor assembly of Example 12, wherein the navigation guidewire further comprises a position sensor and a flexible electrical conduit assembly, wherein the position sensor is located distally relative to the flexible electrical conduit assembly.

Example 14

The image guided adaptor assembly of Example 13, further comprising a coupling unit configured to attach to a proximal end of the flexible electrical conduit assembly, wherein the coupling unit is configured to establish communication between the position sensor and a processing unit.

Example 15

The image guided adaptor assembly of any one or more of Examples 12 through 14, wherein the wire retainer clip defines a first through hole and a second through hole, wherein the first through hole is configured to receive the free end of the shaft, wherein the second through hole is configured to receive the navigation guidewire.

Example 16

The image guided adaptor assembly of Example 15, wherein the first through hole and the second through hole comprises an elastomeric interior surface.

Example 17

The image guided adaptor assembly of any one or more of Examples 15 through 16, wherein the first through hole comprises a first pair of resilient arms.

Example 18

The image guided adaptor assembly of any one or more of Examples 15 through 17, wherein the second through hole comprises a second pair of resilient arms.

Example 19

The image guided adaptor assembly of any one or more of Examples 12 through 18, wherein the proximal portion of the adaptor body comprises a guidewire portion and a shaft portion.

Example 20

An image guided instrument assembly, comprising: (a) an instrument body comprising a handle and a shaft, wherein the shaft comprises a free end; (b) a navigation guidewire; (c) a wire retainer clip, wherein the wire retainer clip is configured to couple with the navigation guidewire and the shaft; and (d) an adaptor body, wherein the adaptor body comprises: (i) a proximal portion, wherein the proximal portion comprises a proximal surface, wherein the proximal portion defines a first pathway and a second pathway, wherein the first pathway and the second pathway extend distally from the proximal surface, wherein the first pathway is dimensioned to receive the free end of the shaft, wherein the second pathway is dimensioned to receive a distal end of the navigation guidewire such that the navigation guidewire and the free end of the shaft are fixed relative to each other, and (ii) a distal portion attached to the proximal portion, wherein the distal portion comprises a distal tip terminating at a distal end, wherein the second pathway extends from the proximal portion into the distal tip.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
  (a) a proximal portion, wherein the proximal portion comprises a proximal surface, wherein the proximal portion defines a first pathway and a second pathway, wherein the first pathway and the second pathway extend distally from the proximal surface, wherein the first pathway comprises a first distal end, wherein the second pathway comprises a second distal end, wherein the first pathway is dimensioned to receive a shaft, wherein the second pathway is dimensioned to receive a navigation guidewire; and
  (b) a distal portion attached to the proximal portion, wherein the distal portion comprises a distal tip terminating at a distal end, wherein the second pathway extends from the proximal portion into the distal tip, wherein the first distal end and the second distal end are enclosed by the distal portion.

2. The apparatus of claim 1, wherein the distal end comprises a narrow-pointed tip.

3. The apparatus of claim 1, wherein the distal tip comprises a spoon-like shape.

4. The apparatus of claim 1, wherein the proximal portion and the distal portion formed from a first material.

5. The apparatus of claim 4, wherein the first material is flexible enough to suitably attach to the shaft and the navigation guidewire.

6. The apparatus of claim 1, wherein the first pathway terminates into a first surface.

7. The apparatus of claim 6, wherein the second pathway terminates into a second surface, wherein the second surface is distal relative to the first surface.

8. The apparatus of claim 7, wherein the second surface is located within the distal tip.

9. An image guided adaptor assembly configured to couple with an instrument, the image guided adaptor assembly comprising:
  (a) a navigation guidewire;
  (b) a wire retainer clip, wherein the wire retainer clip is configured to couple with the navigation guidewire and a shaft of the instrument;
  (c) an adaptor body, wherein the adaptor body comprises:
    a proximal portion, wherein the proximal portion comprises a proximal surface, wherein the proximal portion defines a first pathway and a second pathway, wherein the first pathway and the second pathway extend distally from the proximal surface, wherein the first pathway is dimensioned to receive a free end of the shaft, wherein the second pathway is dimensioned to receive a distal end of the navigation guidewire such that the navigation guidewire and the free end of the shaft are fixed relative to each other, wherein the second pathway comprises an elastomeric material configured to inhibit the navigation guidewire from moving relative to the adaptor body; and
    (ii) a distal portion attached to the proximal portion, wherein the distal portion comprises a distal tip terminating at a distal end, wherein the second pathway extends from the proximal portion into the distal tip.

10. The image guided adaptor assembly of claim 9, wherein the navigation guidewire further comprises a position sensor and a flexible electrical conduit assembly, wherein the position sensor is located distally relative to the flexible electrical conduit assembly.

11. The image guided adaptor assembly of claim 10, further comprising a coupling unit configured to attach to a proximal end of the flexible electrical conduit assembly, wherein the coupling unit is configured to establish communication between the position sensor and a processing unit.

12. The image guided adaptor assembly of claim 9, wherein the wire retainer clip defines a first through hole and a second through hole, wherein the first through hole is configured to receive the free end of the shaft, wherein the second through hole is configured to receive the navigation guidewire.

13. The image guided adaptor assembly of claim 12, wherein the first through hole and the second through hole comprises an elastomeric interior surface.

14. The image guided adaptor assembly of claim 12, wherein the first through hole comprises a first pair of resilient arms.

15. The image guided adaptor assembly of claim 12, wherein the second through hole comprises a second pair of resilient arms.

16. The image guided adaptor assembly of claim 9, wherein the proximal portion of the adaptor body comprises a guidewire portion and a shaft portion.

17. An image guided instrument assembly, comprising:
 (a) an instrument body comprising a handle and a shaft, wherein the shaft comprises a free end;
 (b) a navigation guidewire;
 (c) a wire retainer clip, wherein the wire retainer clip is configured to couple with the navigation guidewire and the shaft; and
 (d) an adaptor body, wherein the adaptor body comprises:
  a proximal portion, wherein the proximal portion comprises a proximal surface, wherein the proximal portion comprises an elastomeric material that defines a first pathway and a second pathway, wherein the first pathway and the second pathway extend distally from the proximal surface, wherein the first pathway is dimensioned to receive the free end of the shaft, wherein the second pathway is dimensioned to receive a distal end of the navigation guidewire such that the navigation guidewire and the free end of the shaft are fixed relative to each other, wherein the elastomeric material is configured to inhibit movement of the navigation guidewire relative to the adaptor body while the adaptor body is coupled to the navigation guidewire, and
  (ii) a distal portion attached to the proximal portion, wherein the distal portion comprises a distal tip terminating at a distal end, wherein the second pathway extends from the proximal portion into the distal tip.

\* \* \* \* \*